United States Patent
Papaix et al.

(10) Patent No.: US 10,172,566 B2
(45) Date of Patent: Jan. 8, 2019

(54) SYSTEM AND METHOD FOR EVALUATING ACTION CAPACITIES OF AN INDIVIDUAL

(71) Applicant: Airbus Operations SAS, Toulouse (FR)

(72) Inventors: Benoit Papaix, Toulouse (FR); Matthieu Pujos, Toulouse (FR)

(73) Assignee: AIRBUS OPERATIONS SAS, Toulouse (FR)

( * ) Notice: Subject to any disclaimer, the term of this patent is extended or adjusted under 35 U.S.C. 154(b) by 0 days.

(21) Appl. No.: 15/596,686

(22) Filed: May 16, 2017

(65) Prior Publication Data
US 2017/0332975 A1 Nov. 23, 2017

(30) Foreign Application Priority Data
May 18, 2016 (FR) ..................... 16 54426

(51) Int. Cl.
*G08B 23/00* (2006.01)
*A61B 5/00* (2006.01)
(Continued)

(52) U.S. Cl.
CPC .......... *A61B 5/7271* (2013.01); *A61B 5/0002* (2013.01); *A61B 5/18* (2013.01);
(Continued)

(58) Field of Classification Search
CPC ... A61B 5/7271; A61B 5/0002; A61B 5/1123; A61B 5/4863; A61B 5/4845;
(Continued)

(56) References Cited

U.S. PATENT DOCUMENTS 6,512,522 B1 * 1/2003 Miller ................... G06T 11/203
345/474
2003/0163057 A1 8/2003 Flick et al.
(Continued)

FOREIGN PATENT DOCUMENTS

WO 2016028228 2/2016

OTHER PUBLICATIONS

French Search Report, dated Feb. 1, 2017, priority document.

*Primary Examiner* — Anh V La
(74) *Attorney, Agent, or Firm* — Greer, Burns & Crain, Ltd.

(57) ABSTRACT

A system for evaluating the action capacities of an individual comprising at least one measurement module, each measurement module being configured to produce at least one measurement point of a physiological parameter of the individual; a computation module configured to determine at least one set of measurement points representative of a distribution law for the measurement point or points, termed measured set; a computation module configured to compute at least one conditional probability of having one or more states of health; a third computation module configured to compute an average of the computed conditional probability or probabilities; a fourth computation module configured to determine at least one level of action capacity of the individual; a transmission module configured to transmit a signal representative of the level or levels of action capacity of the individual to a user device.

10 Claims, 5 Drawing Sheets

(51) Int. Cl.
*G06N 7/00* (2006.01)
*A61B 5/18* (2006.01)
*G06F 19/00* (2018.01)
*G16H 50/30* (2018.01)

(52) U.S. Cl.
CPC ............ *A61B 5/7275* (2013.01); *G06F 19/00* (2013.01); *G06N 7/005* (2013.01); *G16H 50/30* (2018.01)

(58) Field of Classification Search
CPC ..... A61B 5/4803; A61B 5/112; A61B 5/0077; A61B 5/0024; A61B 5/7246; A61B 5/082; A61B 5/18; A61B 5/6898; A61B 5/002; A61B 5/7275; G06N 7/005; G10L 25/66; G10L 15/01; G06F 17/30864; G06F 17/30424; G06F 19/00; G06T 19/006; G16H 50/30

USPC .......................... 340/576, 575, 573.1, 573.7
See application file for complete search history.

(56) References Cited

U.S. PATENT DOCUMENTS

| | | | |
|---|---|---|---|
| 2010/0274100 A1* | 10/2010 | Behar | A61B 5/0002 600/301 |
| 2011/0015496 A1* | 1/2011 | Sherman | A61B 5/0006 600/301 |
| 2012/0179008 A1 | 7/2012 | Burton | |
| 2014/0167967 A1* | 6/2014 | He | B60Q 9/00 340/576 |
| 2014/0240132 A1* | 8/2014 | Bychkov | A61B 5/18 340/576 |
| 2015/0257681 A1 | 9/2015 | Shuster et al. | |

* cited by examiner

SYSTEM AND METHOD FOR EVALUATING ACTION CAPACITIES OF AN INDIVIDUAL

CROSS-REFERENCES TO RELATED APPLICATIONS

This application claims the benefit of the French patent application No. 1654426 filed on Aug. 10, 2010, the entire disclosures of which are incorporated herein by way of reference.

TECHNICAL FIELD

The present invention relates to a device and a method for evaluating action capacities of an individual, in particular of an aircraft pilot.

BACKGROUND OF THE INVENTION

The action capacities of an aircraft pilot may form part of the criteria making it possible to perform a flight under good conditions. Among the action capacities, there exists, for example, the capacity to manage certain flight controls. A pilot's action capacities may evolve throughout the duration of a flight.

Consequently, it may be useful to ascertain the evolution of a pilot's action capacities so that an action plan can be initiated to replace or assist a pilot who does not have the capacity to perform an action.

However, no means currently exists for precisely ascertaining the evolution of a pilot's action capacities during an aircraft flight.

SUMMARY OF THE INVENTION

An object of the present invention is to remedy this drawback by proposing a method and a device making it possible to evaluate the action capacities of an individual.

For this purpose, the invention relates to a system for evaluating the action capacities of an individual, termed evaluation system.

According to the invention, the evaluation system comprises:

a first memory configured to store a database comprising, for at least one state of health and for at least one physiological parameter, at least one probability law curve, termed expert curve, representative of a probability of having a given state of health as a function of a physiological parameter value;

at least one measurement module, each measurement module being configured to produce at least one measurement point of one or more physiological parameters of the individual and to provide at least one confidence interval of the measurement module or modules;

a second memory configured to store the measurement point or points of the physiological parameter or parameters and the confidence interval or intervals;

a first computation module configured to determine at least one set of measurement points representative of a distribution law for the measurement point or points, termed measured set, each measured set being determined on the basis of the measurement point or points of a physiological parameter and of the confidence interval or intervals;

a second computation module configured to compute, for each of the state or states of health and for each of the measured set or sets, at least one conditional probability of having one or more states of health, each conditional probability being computed for each of the points of the measured set knowing the measurement point or points of the physiological parameter;

a third computation module configured to compute, for each of the state or states of health and for each of the measured set or sets, an average of the conditional probability or probabilities computed by the second computation module;

a fourth computation module configured to determine at least one level of action capacity of the individual as a function of the averages of the conditional probability or probabilities;

a transmission module configured to transmit a signal representative of the level or levels of action capacity of the individual to a user device.

Thus, by virtue of the system, it is possible, by at least computing the conditional probabilities of having one or more predetermined states of health, to ascertain the state of health of an individual, notably of an aircraft pilot, so that an action plan can be implemented, if necessary.

Advantageously, the first computation module is configured to compute each conditional probability for a state of health knowing the measurement point or points of a physiological parameter on the basis of the following relation:

$$P(Cs \mid m1 \cap m2 \cap \ldots \cap mN) = \frac{P(Cs)^N \times \prod_{j=1}^{N} P(Cs \mid mj)}{\sum_{i=1}^{M} \left[ P(Ci)^N \times \prod_{j=1}^{N} P(Ci \mid mj) \right]},$$

in which:

N corresponds to the total number of measurement points of a physiological parameter, mj corresponds to a value of a measurement point j, with j lying between 1 and N, M corresponds to the total number of states of health, Ci corresponds to a state of health i, with i lying between 1 and M, Cs corresponds to a state of health for which the conditional probability is computed, P(Cs) corresponds to the probability of having the state of health Cs, P(Cs|mj) corresponds to the conditional probability of having the state of health Cs knowing the value of the measurement point mj, P(Ci) corresponds to the probability of having a state of health Ci from among the M states of health, P(Ci|mj) corresponds to the conditional probability of having the state of health Ci from among the M states of health knowing the value of the measurement point mj, each conditional probability P(Ci|mj) being determined on the basis of the expert curve or curves stored in the first memory.

According to a particular feature, the evaluation system comprises a fifth computation module configured to compute a confidence index on the basis of the confidence interval or intervals, the fourth computation module being configured to determine the level or levels of action capacity as a function of the averages of the conditional probability or probabilities and of the confidence index.

According to another particular feature, the evaluation system furthermore comprises a sixth computation module configured to determine the expert curve or curves.

Advantageously, the sixth computation module is configured to:

collect standard data corresponding to an expert curve representing a standard value of a physiological parameter as a function of a probability of having a particular state of health from among the state or states of health;

carry out an approximation of the expert curve by at least one Bézier curve;

normalize the approximated expert curve.

Moreover, the evaluation system comprises a learning module configured to weight the expert curve or curves stored in the first memory as a function of real physiological parameters of the individual.

The invention also relates to a method for evaluating the action capacities of an individual, termed evaluation method.

According to the invention, the evaluation method comprises:

a measurement step, implemented by at least one measurement module, comprising producing at least one measurement point for at least one physiological parameter of the individual and in providing at least one confidence interval of the measurement module or modules;

a first computation step, implemented by a first computation module, comprising computing at least one set representative of a distribution law for the measurement point or points, termed measured set, the measured set or sets being determined on the basis of the measurement point or points of each of the physiological parameter or parameters and of the confidence interval or intervals;

a second computation step, implemented by a second computation module, comprising computing, for at least one state of health and for each of the measured set or sets, at least one conditional probability of having the or one of the states of health, each conditional probability being computed at each of the points of the measured set knowing the measurement point or points of the physiological parameter;

a third computation step, implemented by a third computation module, comprising computing, for each of the state or states of health and for each of the measured set or sets, an average of the conditional probability or probabilities computed by the second computation module;

a fourth computation step, implemented by a fourth computation module, comprising determining at least one level of action capacity of the individual as a function of the averages of the conditional probabilities;

a transmission step, implemented by a transmission module, comprising transmitting a signal representative of the level or levels of action capacity to a user device.

Advantageously, each conditional probability for a state of health knowing the measurement point or points of a physiological parameter is computed on the basis of the following expression:

$$P(Cs \mid m1 \cap m2 \cap \ldots \cap mN) = \frac{P(Cs)^N \times \prod_{j=1}^{N} P(Cs \mid mj)}{\sum_{i=1}^{M} \left[ P(Ci)^N \times \prod_{j=1}^{N} P(Ci \mid mj) \right]},$$

in which:

N corresponds to the total number of measurement points of a physiological parameter, mj corresponds to a value of a measurement point, M corresponds to the total number of states of health, Ci corresponds to a state of health, $P(Cs \mid m1 \cap m2 \cap \ldots \cap mN)$ corresponds to the conditional probability of having the particular state of health knowing the N measurement points, P(Cs) corresponds to the probability of having a particular state of health Cs, P(Cs|mj) corresponds to the conditional probability of having the particular state of health Cs knowing the value of the measurement point mj, P(Ci) corresponds to the probability of having a state of health Ci from among the M states of health, P(Ci|mj) corresponds to the conditional probability of having the state of health Ci from among the M states of health knowing the measurement mj, each conditional probability P(Ci|mj) being determined on the basis of at least one expert curve stored in a first memory (1).

According to a particular feature, the evaluation method furthermore comprises a fifth computation step, implemented by a fifth computation module, comprising computing a confidence index on the basis of the confidence interval or intervals, the fourth computation step comprising determining at least one action capacity of the individual as a function of the averages of the conditional probabilities and of the confidence index.

According to another particular feature, the evaluation method comprises a sixth computation step, implemented by a sixth computation module, comprising determining the expert curve or curves.

Advantageously, the sixth computation step comprises, for each expert curve:

a sub-step of collecting standard data, the standard data corresponding to an expert curve representing a standard value of a physiological parameter as a function of a probability of having a particular state of health from among the state or states of health;

a sub-step of approximating the expert curve by at least one Bézier curve;

a sub-step of normalizing the approximated expert curve.

Moreover, the evaluation method comprises a learning step, implemented by a learning module, comprising weighting the expert curve or curves stored in the first memory as a function of real physiological parameters of the individual.

BRIEF DESCRIPTION OF THE DRAWINGS

The invention, with its characteristics and advantages, will emerge more clearly on reading the description given with reference to the appended drawings in which.

DETAILED DESCRIPTION OF THE PREFERRED EMBODIMENTS

The subsequent description will refer to the figures cited hereinabove.

Figure 1:
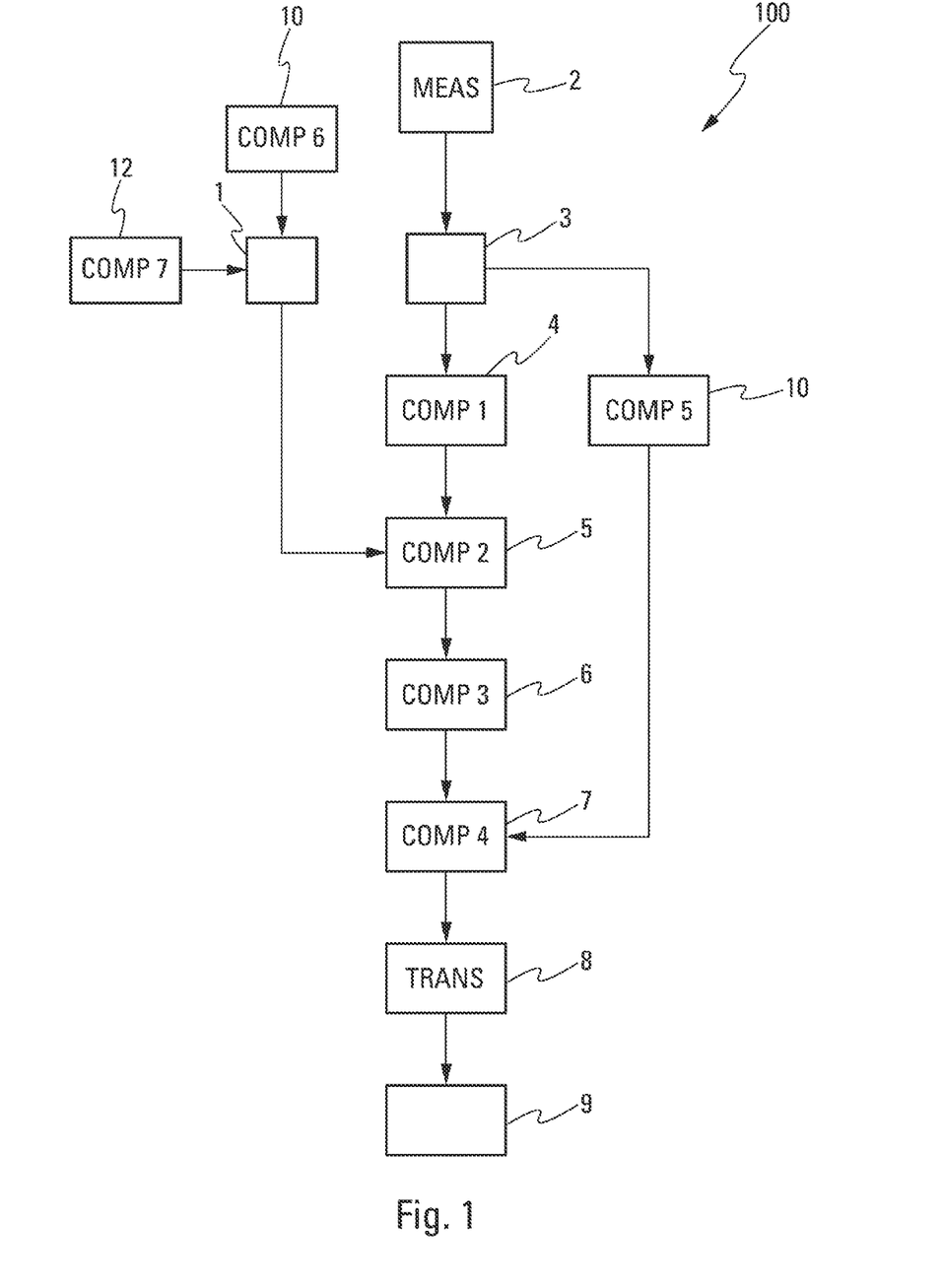
FIG. 1 represents a schematic diagram of the evaluation system.

FIG. 1 illustrates a system for evaluating the action capacities of an individual 100 according to one embodiment. In the subsequent description, the system for evaluating the action capacities of an individual is called the "evaluation system."

The evaluation system 100 corresponds to a data merging system.

The evaluation system 100 comprises a memory 1 configured to store a database.

Figure 3:
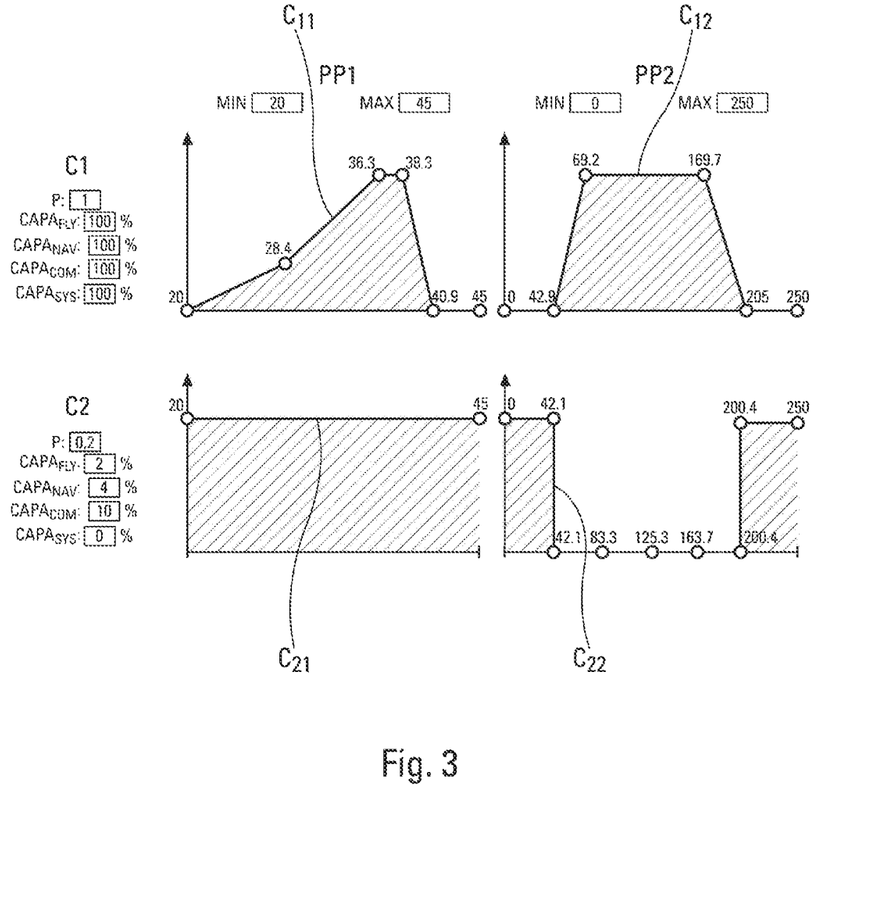
FIG. 3 represents examples of expert curves.

The database contains at least one probability law curve CE11, . . . , CEij, termed expert curve, representative of a probability of having a given state of health as a function of a physiological parameter value (FIG. 3).

By way of example, a physiological parameter PP1, . . . , PPj corresponds to a body temperature, to a heart rate, to a respiratory tempo, to a tracking of the gaze of the individual, to an electroencephalogram or to a level of body movements. The physiological parameters PP1, . . . , PPj are not limited to the physiological parameters given as examples. Other physiological parameters may be used.

A state of health C1, . . . , Ci corresponds, for example, to a normal state of the individual, to a state of sleepiness of the individual or to a state of heart failure of the individual. The states of health C1, . . . , Ci are not limited to the states of health given as examples. Other states of health may be used.

Each expert curve CE11, . . . , CEij is contained in the database for at least one state of health and for at least one physiological parameter.

The evaluation system 100 also comprises at least one measurement module 2 ("MEAS"). Each measurement module 2 is configured to produce at least one measurement point of a physiological parameter PP1, . . . , PPj of the individual. In one embodiment, the measurement module or modules 2 are able to provide a confidence interval of the measurement point or points of the measurement module or modules 2.

By way of example, the measurement module 2 comprises a thermometer able to measure a body temperature or comprises a heart rate monitor able to measure a heart rate. The measurement module 2 is not limited to the measurement modules cited as examples.

According to one variant, a measurement module 2 is configured to measure a single physiological parameter PP1, . . . , PPj. According to another variant, several measurement modules 2 are used to obtain a physiological parameter PP1, . . . , PPj. According to yet another variant, a measurement module 2 is used to obtain several physiological parameters PP1, . . . , PPj. The variants cited hereinabove can be combined together.

Each measurement point corresponds to a value of the physiological parameter PP1, . . . , PPj able to be measured by the measurement module 2 configured to produce each measurement point.

The evaluation system 100 furthermore comprises:

a memory 3 configured to store the measurement point or points of the physiological parameters PP1, . . . , PPj;

a computation module 4 COMP1 configured to determine at least one set of measurement points representative of a distribution law for the measurement point or points, termed measured set, each measured set being determined on the basis of the measurement point or points of a physiological parameter PP1, . . . , PPj and of the confidence interval or intervals;

a computation module 5 COMP2 configured to compute, for the or each of the states of health C1, . . . , Ci and for the or each of the measured sets, at least conditional probabilities of having the state of health or one of the states of health C1, . . . , Ci, each conditional probability being computed at each of the points of the measured set knowing the measurement point or points of the physiological parameter PP1, . . . , PPj;

a computation module 6 COMP3 configured to compute, for the or each of the states of health C1, . . . , Ci and for the or each of the measured sets, an average of the conditional probability or probabilities computed by the computation module 5;

a computation module 7 COMP4 configured to determine at least one level of action capacity of the individual CAPAFLY, CAPANAV, CAPACOM, CAPASYS as a function of the averages of the conditional probability or probabilities;

a transmission module 8 TRANS configured to transmit a signal representative of the level or levels of action capacity of the individual CAPAFLY, CAPANAV, CAPACOM, CAPASYS to a user device 9.

According to one embodiment, the memory 3 is configured to also store the confidence intervals of the measurement point or points.

According to one embodiment, the computation module 4 is configured to compute each conditional probability for a state of health C1, . . . , Ci knowing the measurement point or points of a physiological parameter on the basis of the following relation:

$$P(Cs \mid m1 \cap m2 \cap \ldots \cap mN) = \frac{P(Cs)^N \times \prod_{j=1}^{N} P(Cs \mid mj)}{\sum_{i=1}^{M} \left[ P(Ci)^N \times \prod_{j=1}^{N} P(Ci \mid mj) \right]},$$

in which:

N corresponds to the total number of measurement points of a physiological parameter PP1, . . . , PPj, mj corresponds to a value of a measurement point j, with j lying between 1 and N, M corresponds to the total number of states of health, Ci corresponds to a state of health i, with i lying between 1 and M, Cs corresponds to a state of health for which the conditional probability is computed, P(Cs) corresponds to the probability of having the state of health Cs, P(Cs|mj) corresponds to the conditional probability of having the state of health Cs knowing the value of the measurement point mj, P(Ci) corresponds to the probability of having a state of health Ci from among the M states of health, P(Ci|mj) corresponds to the conditional probability of having the state of health Ci from among the M states of health knowing the value of the measurement point mj.

Each conditional probability P(Ci|mj) is determined on the basis of the expert curve or curves CE11, . . . , CEij stored in the memory 1.

Thus, the evaluation of the state of health of the individual is based on the use of Bayesian classifiers for which the conditional probabilities are given by the conditional probabilities determined on the basis of the expert curves CE11, . . . , CEij.

According to one embodiment, the evaluation system 100 also comprises a computation module 10 COMP5 configured to compute a confidence index IC on the basis of the confidence interval or intervals. The computation module 7 then being configured to determine the level or levels of action capacity CAPAFLY, CAPANAV, CAPACOM, CAPASYS as a function of the averages of the conditional probability or probabilities and of the confidence index IC. According to a variant, the confidence index IC is computed on the basis of the operating state of the measurement module or modules 2. If a measurement module 2 is not operating or is not providing any measurement point, the confidence index IC is weighted to take account of the non-operation or of the non-provision of the measurement module 2.

The confidence indices IC make it possible to determine the reliability of the averages of the conditional probability or probabilities.

Figure 4A:
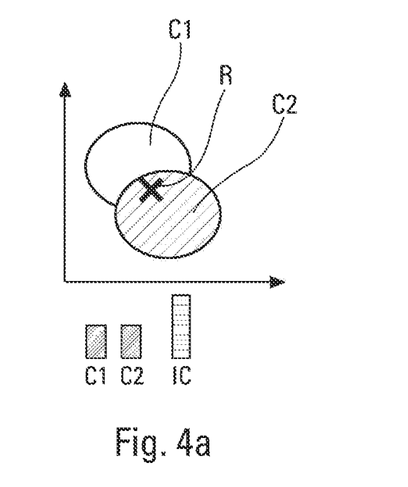
FIGS. 4a to 4d show the influence of the confidence index on the levels of action capacity.
Figure 4B:
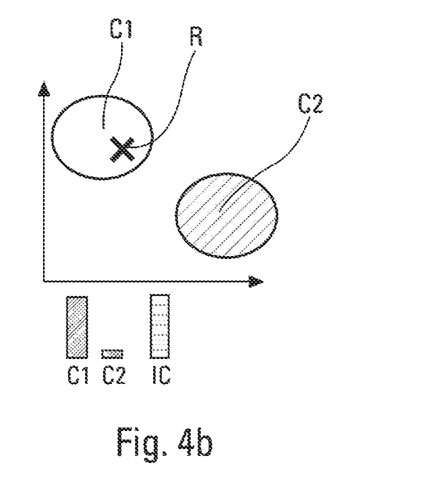
Figure 4C:
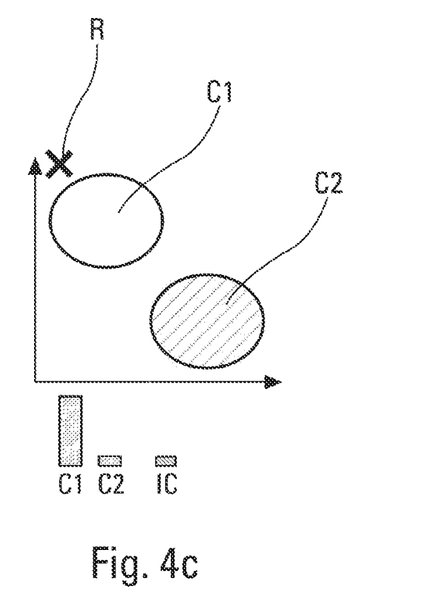
Figure 4D:
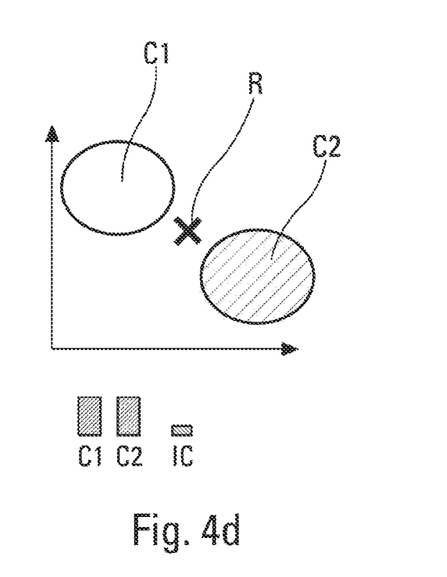

FIGS. 4a to 4d show diagrammatically the influence of the confidence index IC on the levels of action capacity CAPAFLY, CAPANAV, CAPACOM, CAPASYS. Each circle represents a confidence index for a state of health C1 and a state of health C2. The cross R represents the probability of having a state of health. In FIG. 4a, the position of the cross R shows that the individual has the state of health C1 and the state of health C2 with a high confidence index IC. In FIG. 4b, the position of the cross R shows that the individual has the state of health C1 and does not have the state of health C2 with a high confidence index IC. In FIG. 4c, the position of the cross R shows that the individual has the state of health C1 and does not have the state of health C2 with a low confidence index IC. In FIG. 4d, the position of the cross R shows that the individual has the state of health C1 and the state of health C2 with a low confidence index IC.

Figure 5:
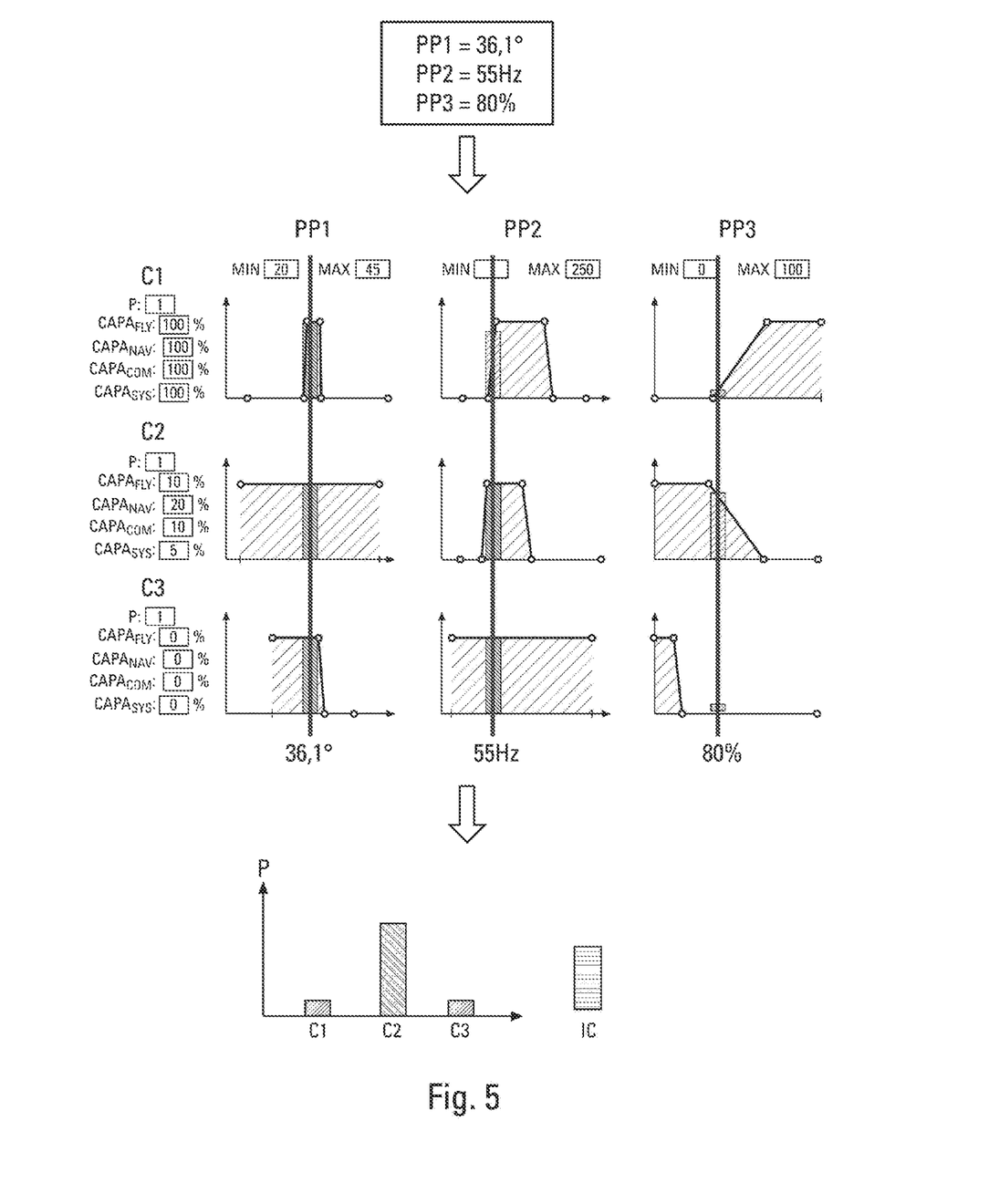
FIG. 5 shows a use of the expert curves.

FIG. 5 shows diagrammatically the use of the expert curves CE11, ..., CEij in accordance with an example. In this example, the physiological parameters correspond to the body temperature PP1 of the individual, the heart rate PP2 and the level of activity PP3. The measurement modules 2 have detected a body temperature of 36.1° C., a heart rate of 55 Hz and a level of activity of 80%. By virtue of the expert curves CE11, ..., CEij, the evaluation system 100 makes it possible to ascertain the probabilities that the individual has of having the state of health C1, C2 or C3. In accordance with the example, the individual has the state of health C1 with a low probability; he has the state of health C2 with a high probability; and he has the state of health C3 with a low probability. The confidence index IC is high enough for these probabilities to be reliable.

According to one embodiment, the evaluation system 100 furthermore comprises a computation module 11 COMP6 configured to determine the expert curve or curves CE11, ..., CEij.

According to a particular feature, for each expert curve CE11, ..., CEij, the computation module 11 is configured to:

collect standard data corresponding to an expert curve CE11, ..., CEij representing a standard value of a physiological parameter as a function of a probability of having a particular state of health from among the state or states of health C1, ..., Ci;

carry out an approximation of the expert curve CE11, ..., CEij by at least one Bézier curve;

normalize the approximated expert curve.

The expert curve CE11, ..., CEij thus obtained is then stored in the database of the memory 1.

By way of example, the expert curves CE11, ..., CEij can be collected in the guise of interactive forms (FIG. 3).

Carrying out the approximation of the expert curve CE11, ..., CEij by at least one Bézier curve makes it possible to avoid zero conditional probabilities and the "corners" for which the curve changes direction abruptly at a point. Such a point corresponds for example to a cusp point or a corner point.

The expert curve CE11, ..., CEij thus approximated corresponds to a probability density. The approximated expert curve CE11, ..., CEij is normalized so that its integral is equal to 1.

Thus, on the basis of the expert curves CE11, ..., CEij obtained, it is possible to determine the conditional probability $P(Ci|mj)$.

Advantageously, the evaluation system 100 comprises a learning module 12 COMP7 configured to weight the expert curve or curves CE11, ..., CEij stored in the memory 1 as a function of the individual's real physiological parameters.

According to a variant, the individual's real physiological parameters are determined on the basis of physiological parameters measured over a period during which the individual is in a state of health that corresponds to a normal state.

According to another variant, the individual's real physiological parameters are determined on the basis of errors in determining the individual's levels of action capacities CAPAFLY, CAPANAV, CAPACOM, CAPASYS. Indeed, for certain physiological parameters, the standard values of these physiological parameters may not be suitable for the individual; this may be a source of errors in determining the levels of action capacities. The expert curves CE11, ..., CEij can then be weighted to take account of these errors.

The transmission module 8 of the evaluation system 100 is configured to transmit a signal representative of the level or levels of action capacity CAPAFLY, CAPANAV, CAPACOM, CAPASYS of the individual to a user device 9.

Thus, by virtue of the learning module 12, the expert curves CE11, ..., CEij are suitable for the individual whose levels of action capacity CAPAFLY, CAPANAV, CAPACOM, CAPASYS are evaluated (FIG. 3).

According to a particular feature, each level of capacity CAPAFLY, CAPANAV, CAPACOM, CAPASYS is associated with an action. By way of example, the action corresponds to the task or to the tasks that the individual is supposed to execute during an aircraft flight (level of action capacity CAPAFLY), for the navigation of the aircraft (level of action capacity CAPANAV), for using a communication module of the aircraft (level of action capacity CAPACOM) or for managing the aircraft's system as a whole (level of action capacity CAPASYS).

According to the levels of action capacity CAPAFLY, CAPANAV, CAPACOM, CAPASYS, an action plan can be defined. By way of example, the action plan comprises the possibility of involving backup means or of taking over from the individual.

According to one embodiment, the modules COMP1, COMP2, COMP3, COMP4, COMP5, COMP6, COMP7, TRANS are integrated into a central unit or a computer.

By way of example, the modules can correspond to algorithms implemented in a software manner in the central unit.

In particular, the modules can be stored in at least one memory area of the central unit.

Figure 2:
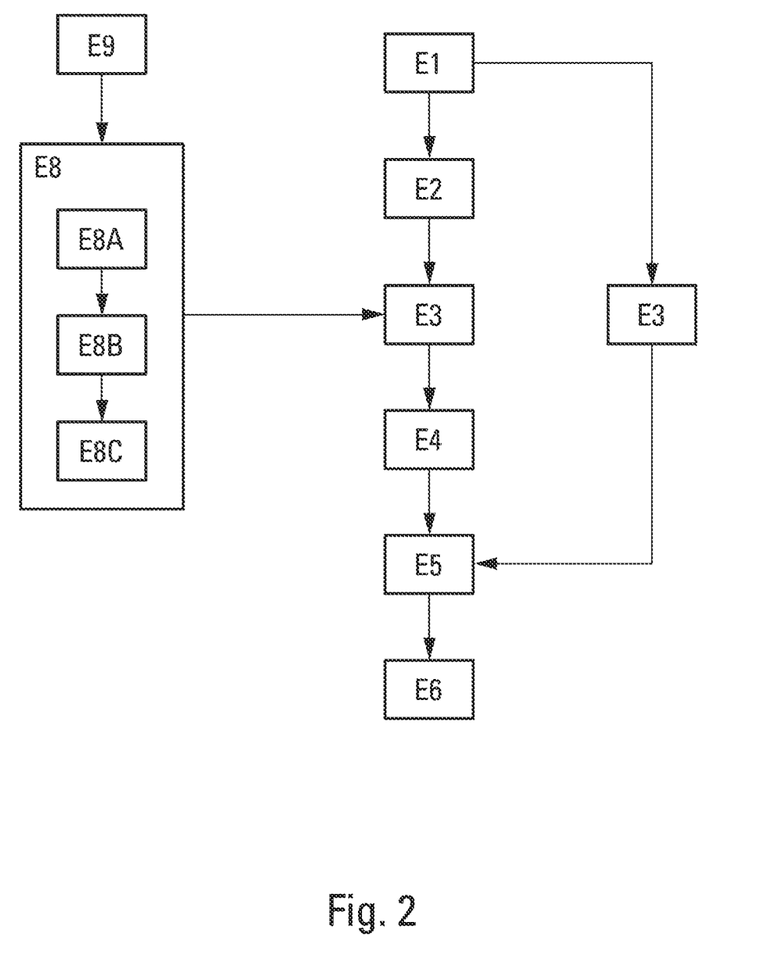
FIG. 2 represents a schematic diagram of the evaluation method.

The evaluation system, such as described hereinabove, implements all of the following steps of a method for evaluating the action capacities of an individual (FIG. 2).

The evaluation method comprises:

a measurement step E1, implemented by at least one measurement module 2, comprising producing at least one measurement point of a physiological parameter PP1, ..., PPj of the individual and in providing at least one confidence interval of the measurement module or modules 2;

a computation step E2, implemented by a computation module 4, comprising computing at least one set representative of a distribution law for the measurement point or points, termed measured curve set, the measured set or sets being determined on the basis of the measurement point or points of each of the physiological parameter or parameters PP1, ..., PPj and of the confidence interval or intervals;

a computation step E3, implemented by a computation module 5, comprising computing, for at least one state of health C1, ..., Ci and for the or each of the measured sets, at least one conditional probability of having the state of health or one of the states of health, each conditional probability being computed at each of the points of the measured set knowing the measurement point or points of the physiological parameter PP1, ..., PPj;

a computation step E4, implemented by a computation module 6, comprising computing, for the or each of the states of health C1, ..., Ci and for the or each of the measured sets, an average of the conditional probability or probabilities computed by the computation module 5;

a computation step E5, implemented by a computation module 7, comprising determining at least one level of action capacity CAPAFLY, CAPANAV, CAPACOM, CAPASYS of the individual as a function of the averages of the conditional probabilities;

a transmission step E6, implemented by a transmission module 8, comprising transmitting a signal representative of the level or levels of action capacity CAPAFLY, CAPANAV, CAPACOM, CAPASYS to a user device 9.

According to one embodiment, the evaluation method comprises a computation step E7, implemented by a computation module 10, comprising computing a confidence index IC on the basis of the confidence interval or intervals. The computation step E5 thus comprises determining at least one level of action capacity CAPAFLY, CAPANAV, CAPACOM, CAPASYS of the individual as a function of the averages of the conditional probabilities and of the confidence index IC.

According to a particular feature, the evaluation method comprises a computation step E8, implemented by a computation module 11, comprising determining the expert curve or curves CE11, ..., CEij.

Advantageously, the computation step E8 comprises for each expert curve CE11, ..., CEij:

a sub-step E8A of collecting standard data, the standard data corresponding to an expert curve CE11, ..., CEij representing a standard value of a physiological parameter as a function of a probability of having a particular state of health C1, ..., Ci from among the state or states of health;

a sub-step E8B of approximating the expert curve CE11, ..., CEij by a Bézier curve;

a sub-step E8C of normalizing the expert curve CE11, ..., CEij.

According to a particular feature, the evaluation method comprises a learning step E9, implemented by a learning module 12, comprising weighting the expert curve or curves CE11, ..., CEij stored in the memory 1 as a function of real parameters of the individual.

While at least one exemplary embodiment of the present invention(s) is disclosed herein, it should be understood that modifications, substitutions and alternatives may be apparent to one of ordinary skill in the art and can be made without departing from the scope of this disclosure. This disclosure is intended to cover any adaptations or variations of the exemplary embodiment(s). In addition, in this disclosure, the terms "comprise" or "comprising" do not exclude other elements or steps, the terms "a" or "one" do not exclude a plural number, and the term "or" means either or both. Furthermore, characteristics or steps which have been described may also be used in combination with other characteristics or steps and in any order unless the disclosure or context suggests otherwise. This disclosure hereby incorporates by reference the complete disclosure of any patent or application from which it claims benefit or priority.

The invention claimed is:
1. A system for evaluating action capacities of an individual, comprising:
a first memory configured to store a database comprising at least one probability law curve (CE11, ... CEij), which is termed an expert curve, representative of a probability of having a given state of health for at least one state of health (C1, ..., Ci) as a function of a physiological parameter value for at least one physiological parameter (PP1, ..., PPj);
at least one measurement module, each measurement module being configured to produce at least one measurement point of a physiological parameter (PP1, ..., PPj) of the individual and to provide at least one confidence interval of the measurement module or modules;
a second memory configured to store the measurement point or points of the physiological parameter or parameters (PP1, ..., PPj) and the confidence interval or intervals;
a first computation module configured to determine at least one set of measurement points representative of a distribution law for the measurement point or points, termed measured set, each measured set being determined on the basis of the measurement point or points of a physiological parameter and of the confidence interval or intervals;
a second computation module configured to compute, for each of the state or states of health (C1, ..., Ci) and for each of the measured set or sets, at least one conditional probability of having one or more states of health, each conditional probability being computed at each of the points of the measured set knowing the measurement point or points of the physiological parameter;
a third computation module configured to compute, for each of the state or states of health (C1, ..., Ci) and for each of the measured set or sets, an average of the conditional probability or probabilities computed by the second computation module;
a fourth computation module configured to determine at least one level of action capacity of the individual (CAPAFLY, CAPANAV, CAPACOM, CAPASYS) as a function of the averages of the conditional probability or probabilities;
a transmission module configured to transmit a signal representative of the level or levels of action capacity of the individual (CAPAFLY, CAPANAV, CAPACOM, CAPASYS) to a user device;
wherein the first computation module is configured to compute each conditional probability for a state of health knowing the measurement point or points of a physiological parameter on the basis of the following relation:

$$P(Cs|m1 \cap m2 \cap \ldots \cap mN) = \frac{P(Cs)^N \times \prod_{j=1}^{N} P(Cs|mj)}{\sum_{i=1}^{M}\left[P(Ci)^N \times \prod_{j=1}^{N} P(Ci|mj)\right]},$$

in which:
- N corresponds to the total number of measurement points of a physiological parameter,
- mj corresponds to a value of a measurement point j, with j lying between 1 and N,
- M corresponds to the total number of states of health,
- Ci corresponds to a state of health i, with i lying between 1 and M,
- Cs corresponds to a state of health for which the conditional probability is computed,
- P(Cs) corresponds to the probability of having the state of health Cs,
- P(Cs|mj) corresponds to the conditional probability of having the state of health Cs knowing the value of the measurement point mj,
- P(Ci) corresponds to the probability of having a state of health Ci from among the M states of health,
- P(Ci|mj) corresponds to the conditional probability of having the state of health Ci from among the M states of health knowing the value of the measurement point mj,
- each conditional probability P(Ci|mj) being determined on the basis of the expert curve or curves (CE11, ... CEij) stored in the first memory (1).

2. The system according to claim 1, further comprising a fifth computation module configured to compute a confidence index on the basis of the confidence interval or intervals, the fourth computation module being configured to determine the level or levels of action capacity (CAPAFLY, CAPANAV, CAPACOM, CAPASYS) as a function of the averages of the conditional probability or probabilities and of the confidence index (IC).

3. The system according to claim 1, further comprising a sixth computation module configured to determine the expert curve or curves (CE11, ... CEij).

4. The system according to claim 3, wherein the sixth computation module is configured to:
- collect standard data corresponding to an expert curve (CE11, ... CEij) representing a standard value of a physiological parameter as a function of a probability of having a particular state of health from among the state or states of health (C1, ... , Ci);
- carry out an approximation of the expert curve (CE11, ... CEij) by at least one Bézier curve;
- normalize the approximated expert curve (CE11, ... CEij).

5. The system according to claim 1, further comprising a learning module configured to weight the expert curve or curves (CE11, ... CEij) stored in the first memory as a function of real physiological parameters of the individual.

6. A method for evaluating action capacities of an individual, comprising:
- implementing a measurement step, by at least one measurement module, comprising producing at least one measurement point for at least one physiological parameter (PP1, ... , PPj) of the individual and providing at least one confidence interval of the measurement module or modules;
- implementing a first computation step, by a first computation module, comprising computing at least one set representative of a distribution law for the measurement point or points, termed measured set, the measured set or sets being determined on the basis of the measurement point or points of each of the physiological parameter or parameters (PP1, ... , PPj) and of the confidence interval or intervals;
- implementing a second computation step, by a second computation module, comprising computing, for at least one state of health (C1, ... , Ci) and for each of the measured set or sets, at least one conditional probability of having one or more states of health (C1, ... , Ci), each conditional probability being computed at each of the points of the measured set knowing the measurement point or points of the physiological parameter (PP1, ... , PPj);
- implementing a third computation step, by a third computation module, comprising computing, for each of the state or states of health (C1, ... , Ci) and for each of the measured set or sets, an average of the conditional probability or probabilities computed by the second computation module;
- implementing a fourth computation step, by a fourth computation module, comprising determining at least one level of action capacity of the individual (CAPAFLY, CAPANAV, CAPACOM, CAPASYS) as a function of the averages of the conditional probabilities;
- implementing a transmission step, by a transmission module, comprising transmitting a signal representative of the level or levels of action capacity (CAPAFLY, CAPANAV, CAPACOM, CAPASYS) to a user device;

wherein each conditional probability for a state of health knowing the measurement point or points of a physiological parameter is computed on the basis of the following expression:

$$P(Cs|m1 \cap m2 \cap \ldots \cap mN) = \frac{P(Cs)^N \times \prod_{j=1}^{N} P(Cs|mj)}{\sum_{i=1}^{M}\left[P(Ci)^N \times \prod_{j=1}^{N} P(Ci|mj)\right]},$$

in which:
- N corresponds to the total number of measurement points of a physiological parameter,
- mj corresponds to a value of a measurement point,
- M corresponds to the total number of states of health,
- Ci corresponds to a state of health,
- P(Cs|m1∩m2∩ ... ∩mN) corresponds to the conditional probability of having the particular state of health knowing the N measurement points,
- P(Cs) corresponds to the probability of having a particular state of health Cs,
- P(Cs|mj) corresponds to the conditional probability of having the particular state of health Cs knowing the value of the measurement point mj,
- P(Ci) corresponds to the probability of having a state of health Ci from among the M states of health,
- P(Ci|mj) corresponds to the conditional probability of having the state of health Ci from among the M states of health knowing the measurement mj,
- each conditional probability P(Ci|mj) being determined on the basis of at least one expert curve (CE11, ... CEij) stored in a first memory (1).

7. The method according to claim 6, further implementing a fifth computation step, by a fifth computation module, comprising computing a confidence index (IC) on the basis of the confidence interval or intervals, the fourth computation step comprising determining at least one action capacity of the individual (CAPAFLY, CAPANAV, CAPACOM, CAPASYS) as a function of the averages of the conditional probabilities and of the confidence index (IC).

8. The method according to claim 6, further implementing a sixth computation step, by a sixth computation module, comprising determining the expert curve or curves.

9. The method according to claim 8, wherein the sixth computation step comprises for each expert curve:
- a sub-step of collecting standard data, the standard data corresponding to an expert curve (CE11, . . . , CEij) representing a standard value of a physiological parameter (PP1, . . . , PPj) as a function of a probability of having a particular state of health from among the state or states of health (C1, . . . , Ci);
- a sub-step of approximating the expert curve (CE11, . . . , CEij) by at least one Bézier curve;
- a sub-step of normalizing the approximated expert curve (CE11, . . . , CEij).

10. The method according to claim 6, further implementing a learning step, by a learning module, comprising weighting the expert curve or curves (CE11, . . . CEij) stored in the first memory as a function of real physiological parameters of the individual.

* * * * *